(12) United States Patent
Meloul

(10) Patent No.: US 9,668,639 B2
(45) Date of Patent: Jun. 6, 2017

(54) BRONCHOSCOPE ADAPTER AND METHOD

(75) Inventor: Raphael Meloul, Caesarea (IL)

(73) Assignee: COVIDIEN LP, Mansfield, MA (US)

( * ) Notice: Subject to any disclaimer, the term of this patent is extended or adjusted under 35 U.S.C. 154(b) by 164 days.

(21) Appl. No.: 13/492,740

(22) Filed: Jun. 8, 2012

(65) Prior Publication Data

US 2012/0253118 A1    Oct. 4, 2012

Related U.S. Application Data

(62) Division of application No. 12/233,933, filed on Sep. 19, 2008, now Pat. No. 8,905,920.

(60) Provisional application No. 60/975,784, filed on Sep. 27, 2007.

(51) Int. Cl.
| | | |
|---|---|---|
| *A61B 1/00* | (2006.01) | |
| *A61B 1/012* | (2006.01) | |
| *A61B 1/267* | (2006.01) | |
| *A61B 1/018* | (2006.01) | |
| *A61B 1/04* | (2006.01) | |

(52) U.S. Cl.
CPC ...... *A61B 1/00128* (2013.01); *A61B 1/00133* (2013.01); *A61B 1/00137* (2013.01); *A61B 1/012* (2013.01); *A61B 1/018* (2013.01); *A61B 1/2676* (2013.01)

(58) Field of Classification Search
CPC ............ A61B 1/00137; A61B 1/00121; A61B 1/00124; A61B 1/00126; A61B 1/00128
USPC .................................. 600/104, 106, 154, 153
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |

(Continued)

FOREIGN PATENT DOCUMENTS

| | | |
|---|---|---|
| CA | 964149 | 3/1975 |
| DE | 3042343 A1 | 6/1982 |

(Continued)

OTHER PUBLICATIONS

European Patent Office, Decision to Grant dated Apr. 13, 2012 in European Patent Application No. 10191689, 1 page.

(Continued)

*Primary Examiner* — Timothy J Neal

(57) ABSTRACT

A bronchoscope adapter is configured for one hand operation by providing a slide lock that is captured within a housing and a retaining nut that can be operated with a single finger or thumb. Rotation of the retaining nut is eased by isolating rotational force from a compression block with a spacer ring.

8 Claims, 6 Drawing Sheets

(56) References Cited

U.S. PATENT DOCUMENTS

| | | |
|---|---|---|
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | Decant, Jr. et al. |
| 4,447,462 A | 5/1984 | Tafuri et al. |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,607,619 A | 8/1986 | Seike et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Budermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,669,172 A | 6/1987 | Petruzzi |
| 4,673,352 A | 6/1987 | Hansen |
| 4,688,037 A | 8/1987 | Krieg |
| 4,701,049 A | 10/1987 | Beckmann et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,679 A | 3/1989 | Shimonaka et al. |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,951,677 A | 8/1990 | Crowley et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 4,994,069 A | 2/1991 | Ritchart et al. |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,021,888 A | 6/1991 | Kondou et al. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,186 A | 10/1991 | Yamamoto et al. |
| 5,059,789 A | 10/1991 | Salcudean |
| 5,078,140 A | 1/1992 | Kwoh |

(56) References Cited

U.S. PATENT DOCUMENTS

| | | |
|---|---|---|
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vikomerson et al. |
| 5,171,245 A | 12/1992 | Cezana |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,622 A | 7/1993 | Brossoit |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,380,302 A | 1/1995 | Orth |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,474,075 A | 12/1995 | Goldberg et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |
| 5,503,416 A | 4/1996 | Aoki et al. |
| 5,506,102 A | 4/1996 | McDonnell |
| 5,513,637 A | 5/1996 | Twiss et al. |

(56) References Cited

U.S. PATENT DOCUMENTS

| | | |
|---|---|---|
| 5,514,146 A | 5/1996 | Lam et al. |
| 5,515,160 A | 5/1996 | Schulz et al. |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,531,686 A | 7/1996 | Lundquist et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,493 A | 11/1996 | Sauer et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,591,137 A * | 1/1997 | Stevens .................. 604/296 |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,728,047 A | 3/1998 | Egoda |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polyani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,865,726 A | 2/1999 | Katsurada et al. |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,879,499 A | 3/1999 | Corvi |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,893,885 A | 4/1999 | Webster, Jr. |
| 5,904,691 A | 5/1999 | Barnett et al. |
| 5,907,395 A | 5/1999 | Schulz et al. |
| 5,913,820 A | 6/1999 | Bladen et al. |

(56) References Cited

U.S. PATENT DOCUMENTS

| | | |
|---|---|---|
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,086,529 A | 7/2000 | Arndt |
| 6,096,050 A | 8/2000 | Audette |
| 6,104,944 A | 8/2000 | Martinelli |
| 6,112,111 A | 8/2000 | Glantz |
| 6,117,070 A | 9/2000 | Akiba |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,132,402 A * | 10/2000 | Tessmann et al. ............ 604/240 |
| 6,134,003 A | 10/2000 | Tearney et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,200,262 B1 | 3/2001 | Ouchi |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,210,378 B1 | 4/2001 | Ouchi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,246,784 B1 | 6/2001 | Summers et al. |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,351,659 B1 | 2/2002 | Vilsmeier |
| 6,355,027 B1 | 3/2002 | Le et al. |
| 6,366,799 B1 | 4/2002 | Acker et al. |
| 6,368,316 B1 | 4/2002 | Jansen et al. |
| 6,373,240 B1 | 4/2002 | Govari |
| 6,381,485 B1 | 4/2002 | Hunter et al. |
| 6,381,490 B1 | 4/2002 | Ostrovsky |
| 6,422,994 B1 | 7/2002 | Kaneko et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,485,413 B1 | 11/2002 | Boppart et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,547,722 B1 | 4/2003 | Higuma et al. |
| 6,551,325 B2 | 4/2003 | Neubauer et al. |
| 6,579,277 B1 | 6/2003 | Rabiner et al. |
| 6,580,938 B1 | 6/2003 | Acker |
| 6,584,174 B2 | 6/2003 | Schubert et al. |
| 6,585,639 B1 | 7/2003 | Kotmel et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,706,041 B1 | 3/2004 | Costantino |
| 6,711,429 B1 | 3/2004 | Gilboa et al. |
| 6,712,842 B1 | 3/2004 | Gifford, III et al. |
| 6,751,492 B2 | 6/2004 | Ben-Haim |
| 6,770,027 B2 | 8/2004 | Banik et al. |
| 6,788,967 B2 | 9/2004 | Ben-Haim et al. |
| 6,796,963 B2 | 9/2004 | Carpenter et al. |

(56) References Cited

U.S. PATENT DOCUMENTS

| | | |
|---|---|---|
| 6,887,236 B2 | 5/2005 | Gilboa |
| 6,947,788 B2 | 9/2005 | Gilboa et al. |
| 6,960,161 B2 | 11/2005 | Amling et al. |
| 6,995,729 B2 | 2/2006 | Govari et al. |
| 7,022,066 B2 | 4/2006 | Yokoi et al. |
| 7,101,380 B2 | 9/2006 | Khachin et al. |
| 7,182,756 B2 | 2/2007 | Saeed et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,144 B2 * | 6/2010 | Suzuki .................. 600/106 |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 2001/0004676 A1 | 6/2001 | Ouchi |
| 2001/0007918 A1 | 7/2001 | Vilsmeier et al. |
| 2001/0007925 A1 | 7/2001 | Ritchart et al. |
| 2001/0031919 A1 | 10/2001 | Strommer et al. |
| 2001/0034530 A1 | 10/2001 | Malackowski et al. |
| 2001/0036245 A1 | 11/2001 | Kienzle, III et al. |
| 2002/0026097 A1 | 2/2002 | Akiba |
| 2002/0067408 A1 | 6/2002 | Adair et al. |
| 2002/0087100 A1 | 7/2002 | Onuki et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0162555 A1 | 11/2002 | West et al. |
| 2002/0165503 A1 | 11/2002 | Morris et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0028096 A1 | 2/2003 | Niwa et al. |
| 2003/0040657 A1 | 2/2003 | Yamaya et al. |
| 2003/0074011 A1 | 4/2003 | Gilboa et al. |
| 2003/0086599 A1 | 5/2003 | Armato et al. |
| 2003/0114742 A1 | 6/2003 | Lewkowicz et al. |
| 2003/0142753 A1 | 7/2003 | Gunday |
| 2003/0160721 A1 | 8/2003 | Gilboa et al. |
| 2003/0171653 A1 | 9/2003 | Yokoi et al. |
| 2003/0227547 A1 | 12/2003 | Iddan |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2004/0260201 A1 | 12/2004 | Mueller, Jr. |
| 2005/0033149 A1 | 2/2005 | Strommer et al. |
| 2005/0059890 A1 | 3/2005 | Deal et al. |
| 2005/0080342 A1 | 4/2005 | Gilreath et al. |
| 2005/0085715 A1 | 4/2005 | Dukesher et al. |
| 2005/0090818 A1 | 4/2005 | Pike, Jr. et al. |
| 2005/0107688 A1 | 5/2005 | Strommer |
| 2005/0119527 A1 | 6/2005 | Banik et al. |
| 2005/0182292 A1 | 8/2005 | Suzuki |
| 2005/0182295 A1 | 8/2005 | Soper et al. |
| 2005/0197566 A1 | 9/2005 | Strommer et al. |
| 2005/0229934 A1 | 10/2005 | Willeford |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0069313 A1 | 3/2006 | Couvillon, Jr. et al. |
| 2006/0149134 A1 | 7/2006 | Soper et al. |
| 2006/0184016 A1 | 8/2006 | Glossop |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0225559 A1 | 9/2007 | Clerc et al. |
| 2007/0265639 A1 | 11/2007 | Danek et al. |
| 2007/0287901 A1 | 12/2007 | Strommer et al. |
| 2007/0293721 A1 | 12/2007 | Gilboa |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0125760 A1 | 5/2008 | Gilboa |
| 2008/0132757 A1 | 6/2008 | Tgavalekos |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2009/0182224 A1 | 7/2009 | Shmarak et al. |
| 2009/0234223 A1 | 9/2009 | Onoda et al. |
| 2009/0318797 A1 | 12/2009 | Hadani |
| 2010/0016757 A1 | 1/2010 | Greenburg et al. |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19610984 A1 | 9/1997 |
| DE | 19715202 A1 | 10/1998 |

(56) References Cited

FOREIGN PATENT DOCUMENTS

| | | |
|---|---|---|
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0894473 A2 | 8/1994 |
| EP | 0651968 A1 | 5/1995 |
| EP | 0796633 A1 | 9/1997 |
| EP | 0908146 A2 | 10/1997 |
| EP | 0930046 A2 | 11/1997 |
| EP | 0655138 B1 | 4/1998 |
| EP | 0857461 A2 | 8/1998 |
| EP | 0894473 A2 | 2/1999 |
| EP | 1078644 A1 | 8/1999 |
| EP | 1255113 A1 | 6/2002 |
| EP | 1543765 A1 | 6/2005 |
| EP | 1667749 B1 | 8/2009 |
| EP | 2096523 A1 | 9/2009 |
| FR | 2417970 A1 | 9/1979 |
| FR | 2618211 A1 | 1/1989 |
| GB | 2094590 A | 9/1982 |
| GB | 2164856 A | 4/1986 |
| JP | 63-240851 A | 10/1988 |
| JP | 03-267054 A | 11/1991 |
| JP | 06-125869 A | 5/1994 |
| JP | 06194639 A | 7/1994 |
| JP | 07-043619 A | 2/1995 |
| JP | 09-253038 A | 9/1997 |
| JP | 10-197807 A | 7/1998 |
| JP | 2000-075218 A | 3/2000 |
| JP | 2000-279379 A | 10/2000 |
| JP | 2001-231743 A | 8/2001 |
| JP | 2001-275942 A | 10/2001 |
| WO | WO88/09151 A1 | 12/1988 |
| WO | WO89/05123 A1 | 6/1989 |
| WO | WO90/05494 A1 | 5/1990 |
| WO | WO91/03982 A1 | 4/1991 |
| WO | WO91/04711 A1 | 4/1991 |
| WO | WO91/07726 A1 | 5/1991 |
| WO | WO92/03090 A1 | 3/1992 |
| WO | WO92/06645 A1 | 4/1992 |
| WO | WO94/04938 A1 | 3/1994 |
| WO | WO94/23647 A1 | 10/1994 |
| WO | WO94/24933 A1 | 11/1994 |
| WO | WO95/07055 A1 | 3/1995 |
| WO | WO96/11624 A1 | 4/1996 |
| WO | WO96/32059 A1 | 10/1996 |
| WO | WO97/29682 A1 | 8/1997 |
| WO | WO97/29684 A1 | 8/1997 |
| WO | WO97/36192 A1 | 10/1997 |
| WO | WO97/49453 A1 | 12/1997 |
| WO | WO98/08554 A1 | 3/1998 |
| WO | WO98/38908 A1 | 9/1998 |
| WO | WO99/15097 A1 | 4/1999 |
| WO | WO99/21498 A1 | 5/1999 |
| WO | WO99/23956 A1 | 5/1999 |
| WO | WO99/26549 A1 | 6/1999 |
| WO | WO99/27839 A1 | 6/1999 |
| WO | WO99/29253 A1 | 6/1999 |
| WO | WO99/33406 A1 | 7/1999 |
| WO | WO99/37208 A1 | 7/1999 |
| WO | WO99/38449 A1 | 8/1999 |
| WO | WO99/52094 A1 | 10/1999 |
| WO | WO99/60939 A1 | 12/1999 |
| WO | WO00/06701 A1 | 2/2000 |
| WO | WO00/14056 A1 | 3/2000 |
| WO | WO00/16684 A1 | 3/2000 |
| WO | WO00/35531 A1 | 6/2000 |
| WO | WO01/19235 A1 | 3/2001 |
| WO | WO01/30437 A1 | 5/2001 |
| WO | WO01/91842 A1 | 6/2001 |
| WO | WO01/67035 A1 | 9/2001 |
| WO | WO01/87136 A2 | 11/2001 |
| WO | WO01/87398 A2 | 11/2001 |
| WO | WO02/24054 A2 | 3/2002 |
| WO | WO02/064011 A2 | 8/2002 |
| WO | WO02/070047 A1 | 9/2002 |
| WO | WO03/086498 A2 | 10/2003 |
| WO | WO2004/023986 A1 | 3/2004 |
| WO | WO2005/025635 A2 | 3/2005 |
| WO | WO 2005/025635 A2 | 3/2005 |
| WO | WO 2005/046785 A1 | 5/2005 |
| WO | WO2006/116597 A2 | 11/2006 |
| WO | WO2007/109418 A2 | 9/2007 |

OTHER PUBLICATIONS

United States Patent and Trademark Office, Office Action mailed Feb. 22, 2012 in U.S. Appl. No. 12/233,933, 10 pages.
European Patent Office, Extended European Search Report dated Feb. 20, 2012 in European Patent Application No. 06701745, 9 pages.
United States Patent and Trademark Office, Final Office Action mailed Dec. 19, 2011 in U.S. Appl. No. 10/571,793, 8 pages.
European Patent Office, Extended European Search Report dated Nov. 22, 2011 in European Patent Application No. 11182823, 5 pages.
European Patent Office, Extended European Search Report dated Nov. 21, 2011 in European Patent Application No. 11182823, 5 pages.
WIPO, U.S. International Search Authority, International Search Report and Written Opinion mailed Oct. 7, 2011 in International Patent Application No. PCT/US2011/040579, 8 pages.
European Patent Office, Extended European Search Report dated Sep. 6, 2011 in European Patent Application No. 03719056, 6 pages.
European Patent Office, Extended European Search Report dated Sep. 6, 2011 in European Patent Application No. 11174666, 6 pages.
Japanese Patent Office, Official Action dated Aug. 23, 2011 in Japanese Patent Application No. 2007-552806, 7 pages.
Japanese Patent Office, Examiner's Report mailed Aug. 19, 2011 in Japanese Patent Application No. JP2007-552806, 7 pages.
WIPO, U.S. International Preliminary Examining Authority, International Preliminary Report on Patentability mailed Jun. 30, 2011 in International Patent Application No. PCT/US2009/069073, 6 pages.
United States Patent and Trademark Office, Office Action mailed May 24, 2011 in U.S. Appl. No. 10/571,793, 8 pages.
United States Patent and Trademark Office, Office Action mailed Mar. 31, 2011 in U.S. Appl. No. 12/643,917, 10 pages.
European Patent Office, Extended European Search Report dated Mar. 8, 2011 in European Patent Application No. 10191689, 4 pages.
United States Patent and Trademark Office, Office Action mailed Dec. 23, 2010 in U.S. Appl. No. 10/571,793, 11 pages.
European Patent Office, Supplementary European Search Report dated Nov. 15, 2010 in European Patent Application No. EP10159373.9, 12 pages.
United States Patent and Trademark Office, Office Action mailed Oct. 4, 2010 in U.S. Appl. No. 12/271,175, 11 pages.
European Patent Office, Examination Report dated Sep. 11, 2010 in European Patent Application No. 3719056, 4 pages.
United States Patent and Trademark Office, Final Office Action mailed Jun. 23, 2010 in U.S. Appl. No. 10/571,793, 10 pages.
WIPO, U.S. International Search Authority, International Search Report and Written Opinion mailed Apr. 23, 2010 in International Patent Application No. PCT/US2009/069073, 8 pages.
WIPO, U.S. International Preliminary Examining Authority, International Preliminary Report on Patentability mailed Apr. 8, 2010 in International Patent Application No. PCT/IB2008/002543, 7 pages.

(56) References Cited

OTHER PUBLICATIONS

European Patent Office, Examination Report dated Mar. 30, 2010 in European Patent Application No. EP05737664.2, 5 pages.
Japanese Patent Office, Official Action dated Mar. 12, 2010 in Japanese Patent Application No. 2006-526007, 5 pages.
European Patent Office, Extended European Search Report dated Dec. 1, 2009 in European Patent Application No. 09157586, 7 pages.
United States Patent and Trademark Office, Office Action mailed Nov. 27, 2009 in U.S. Appl. No. 10/571,793, 11 pages.
WIPO, U.S. International Search Authority, International Search Report and Written Opinion mailed Nov. 12, 2009 in International Patent Application No. PCT/IL2009/000697, 9 pages.
WIPO, U.S. International Preliminary Examining Authority, International Preliminary Report on Patentability mailed Jul. 28, 2009 in International Patent Application No. PCT/IL2005/000159, 6 pages.
European Patent Office, Examination Report dated Jul. 14, 2009 in European Patent Application No. 03719056, 6 pages.
United States Patent and Trademark Office, Office Action mailed Jun. 24, 2009 in U.S. Appl. No. 10/571,695, 11 pages.
WIPO, U.S. International Preliminary Examining Authority, International Preliminary Report on Patentability mailed Mar. 30, 2009 in International Patent Application No. PCT/IL2006/000113, 6 pages.
WIPO, U.S. International Search Authority, International Search Report and Written Opinion mailed Mar. 16, 2009 in International Patent Application No. PCT/IB2008/002543, 16 pages.
United States Patent and Trademark Office, Final Office Action mailed Mar. 12, 2009 in U.S. Appl. No. 10/597,747, 7 pages.
European Patent Office, Supplementary European Search Report dated Feb. 27, 2009 in European Patent Application No. 03719056, 6 pages.
European Patent Office, Decision to Grant dated Feb. 20, 2009 in European Patent Application No. 04770514, 24 pages.
WIPO, U.S. International Search Authority, International Search Report and Written Opinion mailed Dec. 15, 2008 in International Patent Application No. PCT/IL2006/000113, 6 pages.
Japanese Patent Office, Official Action dated Dec. 12, 2008 in Japanese Patent Application No. 2008-583508, 9 pages.
European Patent Office, Supplementary European Search Report dated Oct. 7, 2008 in European Patent Application No. 04770514, 4 pages.
European Patent Office, Supplementary European Search Report dated Sep. 18, 2008 in European Patent Application No. EP0477514.1, 4 pages.
United States Patent and Trademark Office, Office Action mailed Sep. 11, 2008 in U.S. Appl. No. 10/597,747, 9 pages.
WIPO, U.S. International Search Authority, International Search Report and Written Opinion mailed Jul. 11, 2008 in International Patent Application No. PCT-IL2005/000159, 12 pages.
WIPO, U.S. International Preliminary Examining Authority, International Preliminary Report on Patentability mailed Oct. 9, 2007 in International Patent Application No. PCT/IL2004/000843, 4 pages.
WIPO, U.S. International Search Authority, International Search Report and Written Opinion mailed Sep. 24, 2007 in International Patent Application No. PCT/IL2004/000843, 4 pages.
WIPO, U.S. International Search Authority, International Search Report and Written Opinion mailed Jul. 11, 2007 in International Patent Application No. PCT/IL2005/000159, 6 pages.
United States Patent and Trademark Office, Notice of Allowance mailed Oct. 6, 2006 in U.S. Appl. No. 10/491,099, 7 pages.
China Patent and Trademark Office, Office Action dated Jun. 19, 2006 in Chinese Patent Application No. 038135485, 5 pages.
United States Patent and Trademark Office, Office Action mailed Dec. 30, 2005 in U.S. Appl. No. 10/491,099, 15 pages.
United States Patent and Trademark Office, Office Action mailed Apr. 22, 2005 in U.S. Appl. No. 10/491,099, 5 pages.
United States Patent and Trademark Office, Notice of Allowance mailed Jan. 3, 2005 in U.S. Appl. No. 10/137,415, 9 pages.
Shmarak, I. et al., U.S. Appl. No. 10/986,567, filed Nov. 2004 (abandoned, unpublished), 84 pages.
United States Patent and Trademark Office, Office Action mailed Jul. 1, 2004 in U.S. Appl. No. 10/10,137,415, 14 pages.
WIPO, U.S. International Preliminary Examining Authority, International Preliminary Report on Patentability mailed Jan. 24, 2004 in International Patent Application No. PCT/IL2003/000323, 3 pages.
WIPO, U.S. International Search Authority, International Search Report mailed Dec. 8, 2003 in International Patent Application No. PCT/IL2003/000323, 1 page.
Stenoien, D.L. et al., "Ligand-Mediated Assembly and Real-Time Cellular Dynamics of Estrogen Receptor α-Coactivator Complexes in Living Cells," *Molecular and Cellular Biology*, Jul. 2001, pp. 4404-4412, 9 pages.
McKenna, N.J. et al., "Nuclear Receptor Coregulators: Cellular and Molecular Biology," *Endocrine Reviews* 20(3): 321-344, Jun. 1, 1999, 24 pages.
Ding, X.F. et al., "Nuclear Receptor-Binding Sites of Coactivators Glucocorticoid Receptor Interacting Protein 1 (GRIP1) and Steroid Receptor Coactivator 1 (SRC-1): Multiple Motifs with Different Binding Specificities," *Molecular Endocrinology* 12:302-313, Feb. 1, 1998 (9 pages).
Extended European Search Report dated Jan. 24, 2014 for EP 08 832 799.4.

\* cited by examiner

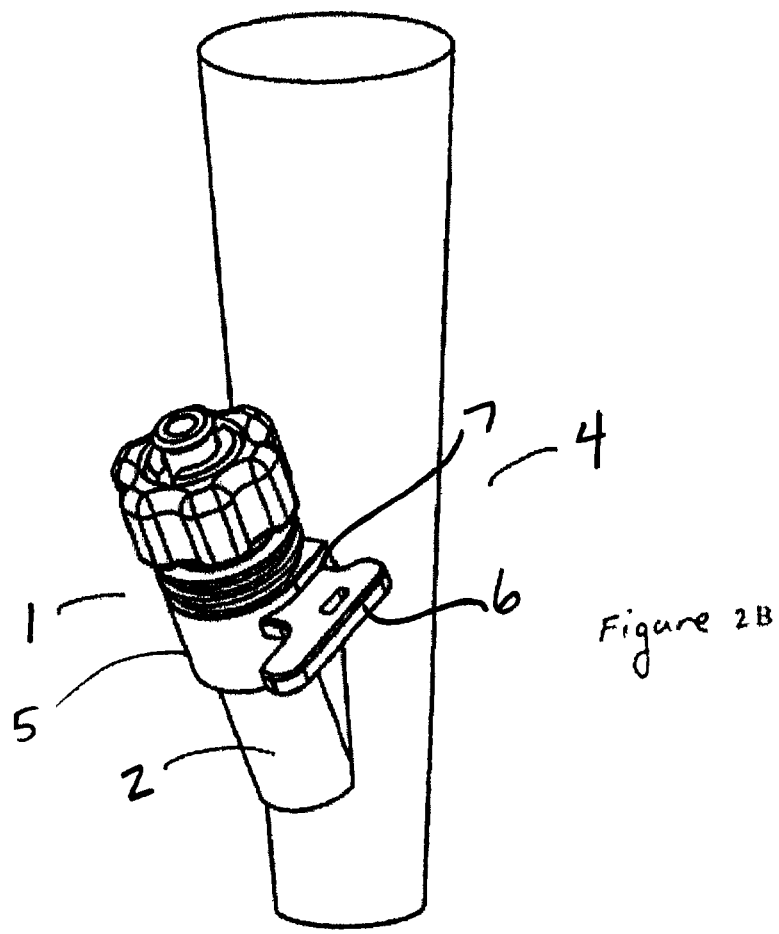
PRIOR ART

BRONCHOSCOPE ADAPTER AND METHOD

RELATED APPLICATIONS

The present invention is a divisional application of U.S. patent application Ser. No. 12/233,933, filed Sep. 19, 2008 now U.S. Pat. No. 8,905,920 entitled Bronchoscope Adapter And Method, which claims benefit of U.S. Provisional Application Ser. No. 60/975,784, filed Sep. 27, 2007 entitled Bronchoscope Adapter, both of which are incorporated herein by reference in their entireties.

BACKGROUND OF THE INVENTION

The present invention relates to bronchoscopy and, in particular, adapters and bronchoscopy-related accessories for use when performing surgical procedures using a bronchoscope.

The most common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen or working channel through which instruments may be inserted, including but not limited to diagnostic (e.g., biopsy tools) and therapeutic (e.g., laser, cryo or RF tissue elimination probes) instruments. The distal tip of a bronchoscope is steerable. Rotating a lever placed at the handle of the bronchoscope actuates a steering mechanism which deflects the tip in one or more directions.

Bronchoscopies are performed by expert pulmonologists, also known as bronchoscopists, and are used routinely in the diagnosis and treatment of conditions such as lung cancer, airway stenosis, and emphysema. Bronchoscopies are typically performed by a staff of at least two persons: the bronchoscopist and at least one assistant, usually a nurse. During a typical procedure, the bronchoscopist holds the bronchoscope handle with one hand and the bronchoscope tube with the other hand. He or she manipulates the distal tip of the bronchoscope inside the lung by rotating a deflection lever and by pushing and pulling the tube. Once the tip is brought to a target, a bronchoscope tool can be inserted into the working channel to perform a diagnostic or therapeutic procedure.

During insertion and operation of the bronchoscopic tool, the distal tip of the bronchoscope should be held steady at the target. Performing all of these tasks concurrently often requires the hands of more than one person. Two hands are needed to secure the bronchoscope in place, and one to two more hands are needed for inserting and actuating the bronchoscopic tool. Performing a procedure that requires two people is generally more expensive and the potential for error is increased. Hence, it is desirable to modify a procedure so that it may be performed with one or two hands, if possible.

Of particular relevance to the present invention is a device and method described in PCT Patent Publication No. WO 03/086498 entitled "Endoscope Structure and Techniques for Navigation in Branched Structure" to Gilboa, which is hereby incorporated by reference in its entirety. This patent application describes a method and apparatus in which a locatable guide ("LG"), enveloped by a sheath, is used to navigate a bronchoscopic tool to a location within the lung. The LG/sheath combination is inserted into the lung via the working channel of a bronchoscope. Once the tip of the guide is located at its target, a lock, which is placed at the orifice ("connection port") of the bronchoscope's working channel, is operated to prevent the sheath from sliding in or out of the bronchoscope. The guide is then withdrawn from the sheath, leaving the sheath in place to guide a tool to the required target location.

One of the many tools often used with a bronchoscope is a vacuum pump. A vacuum pump is used to clear mucus from the airways. In order for the vacuum pump to work properly, it must be attached to the bronchoscope using a connector that will form a seal with the proximal orifice of the working channel. Hence, when transitioning from the use of a locatable guide to the use of a vacuum pump or other tools, a sealing device must be unlocked during the tool exchange and then locked down onto the tool prior to use.

Additionally, because all of the tools used with a bronchoscope are necessarily long and slender, they are inherently flimsy when unsupported. Thus, inserting a tool into a bronchoscope can be difficult or impossible to do quickly with one hand. While this problem can be addressed easily by holding the end of the sheath in one hand and the tool in another, this would again require additional free hands during performance of the procedure.

In order to facilitate operation of a system such as described in the aforementioned application by a single practitioner, it would be preferable to allow the practitioner to temporarily release his or her grip on a secondary tool or device used via the working channel of the bronchoscope. At the same time, it is preferable that the device remains immediately accessible and operable, and does not hang loosely.

There is therefore a need for an adaptor for use with a bronchoscope which would facilitate operation of a bronchoscope and associated tools by a single practitioner. It would also be advantageous to provide an adapter for the connection port of the working channel of a bronchoscope which would perform both the sealing and tool-locking functions without requiring replacement of an attachment during the procedure. It would further be advantageous to provide an arrangement according to the teachings of the aforementioned PCT patent publication which would further facilitate insertion of tools into the guide sheath.

SUMMARY OF THE INVENTION

The present invention relates to an adaptor for use on a bronchoscope handle when performing surgical procedures using a bronchoscope.

One aspect of the present invention provides a sealing and locking adapter for attachment to an access port of a working channel of a bronchoscope to allow insertion and locking of a tool while sealing the access port when not in use. The adapter comprises a housing configured for mating with the access port of the working channel of the bronchoscope. A sealing arrangement deployed within the housing and a clamping arrangement deployed within the housing lock a tool inserted through the housing and into the working channel in position.

BRIEF DESCRIPTION OF THE DRAWINGS

FIG. 2B is a perspective view of a prior art bronchoscope adapter placed on a bronchoscope handle;

DETAILED DESCRIPTION OF THE INVENTION

Figure 1:
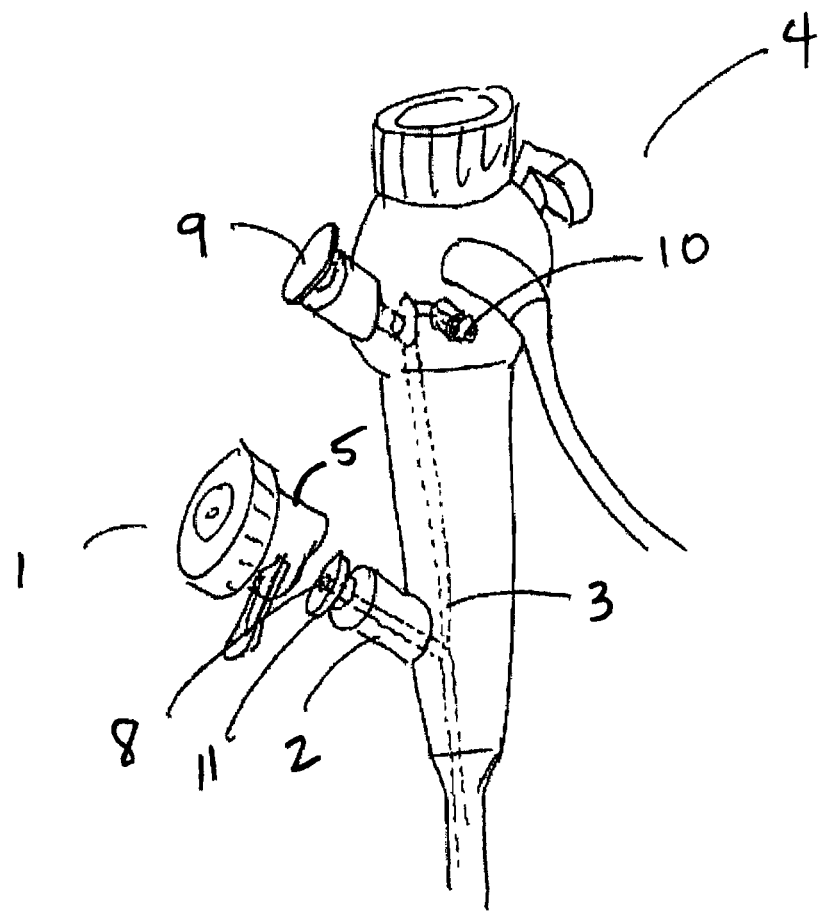
FIG. 1 is a perspective view of a prior art bronchoscope adapter.
Figure 2A:
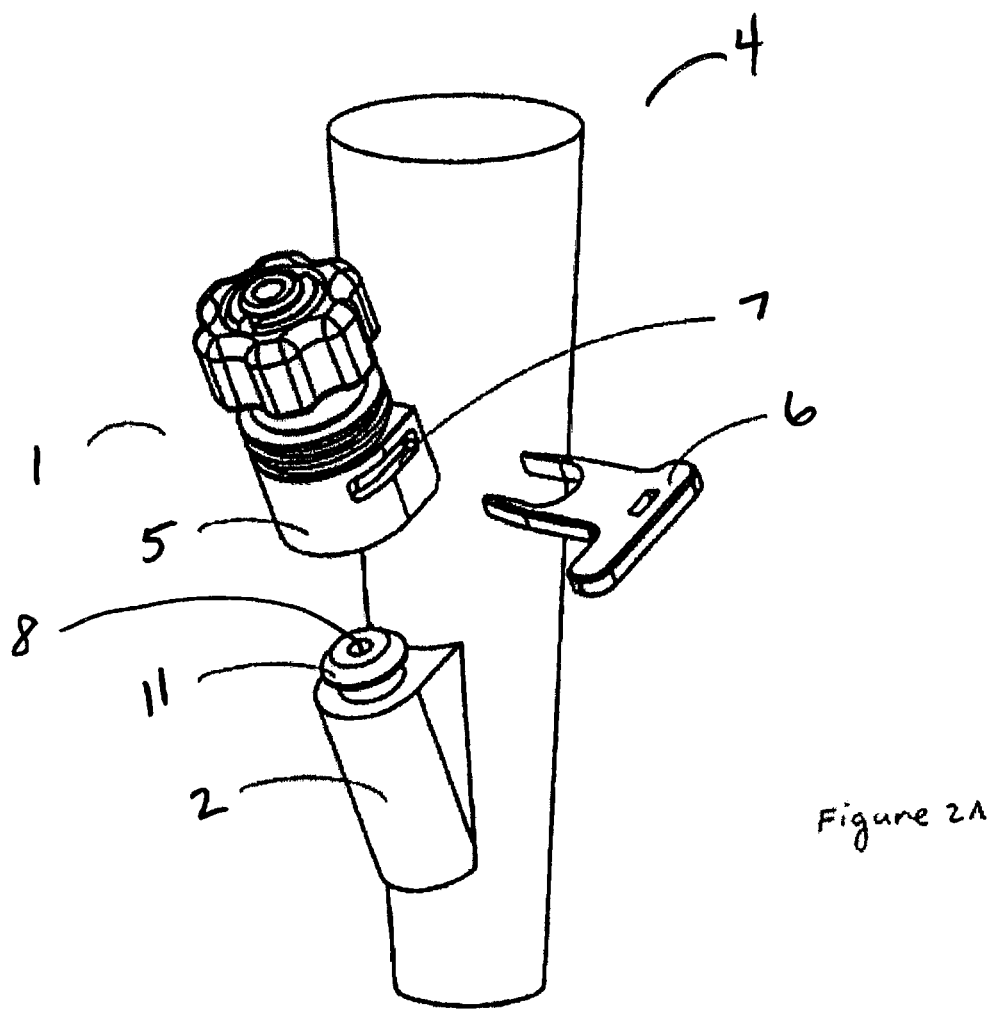
FIG. 2A is a perspective view of a prior art bronchoscope adapter being placed on a bronchoscope handle.

Referring now to Figures, and first to FIGS. 1 and 2, a bronchoscope adapter known in the prior art is shown. The bronchoscope adapter 1 attaches to an access port 2 leading to a working channel 3 inside of a bronchoscope handle 4. The adapter 1 allows the insertion and locking of a tool (not shown) and serves to seal the access port 2 when not in use. The prior art adapter 1 includes a housing 5 configured for mating with the access port 2. The housing 5 is first positioned so as to envelop the access port 2 (FIG. 2a), and then a forked key 6 is inserted into a slot 7 to attach and maintain contact pressure between the adapter 1 and an input orifice 8 that leads to the working channel 3 (FIG. 2b). These prior art devices and methods are described in detail in PCT Patent Publication No. WO05/025635 entitled "System of Accessories for Use with Bronchoscopes" to Greenburg et al., which is herein incorporated by reference in its entirety.

Tools are insertable into the working channel 3 through the input orifice 8. The working channel 3 extends through the entire length of the bronchoscope. The working channel 3 is connectable to a vacuum pump (not shown) or other source of suction through a valve 9 and a second connector 10. For the suction to work properly, the adapter 1 must be sealed. When the valve 9 is pressed open, the pump applies suction through the working channel 3. A gasket fitting 11 is incorporated at the entrance of the working channel 3 on which a rubber gasket can be attached for sealing the orifice 8.

Figure 3:
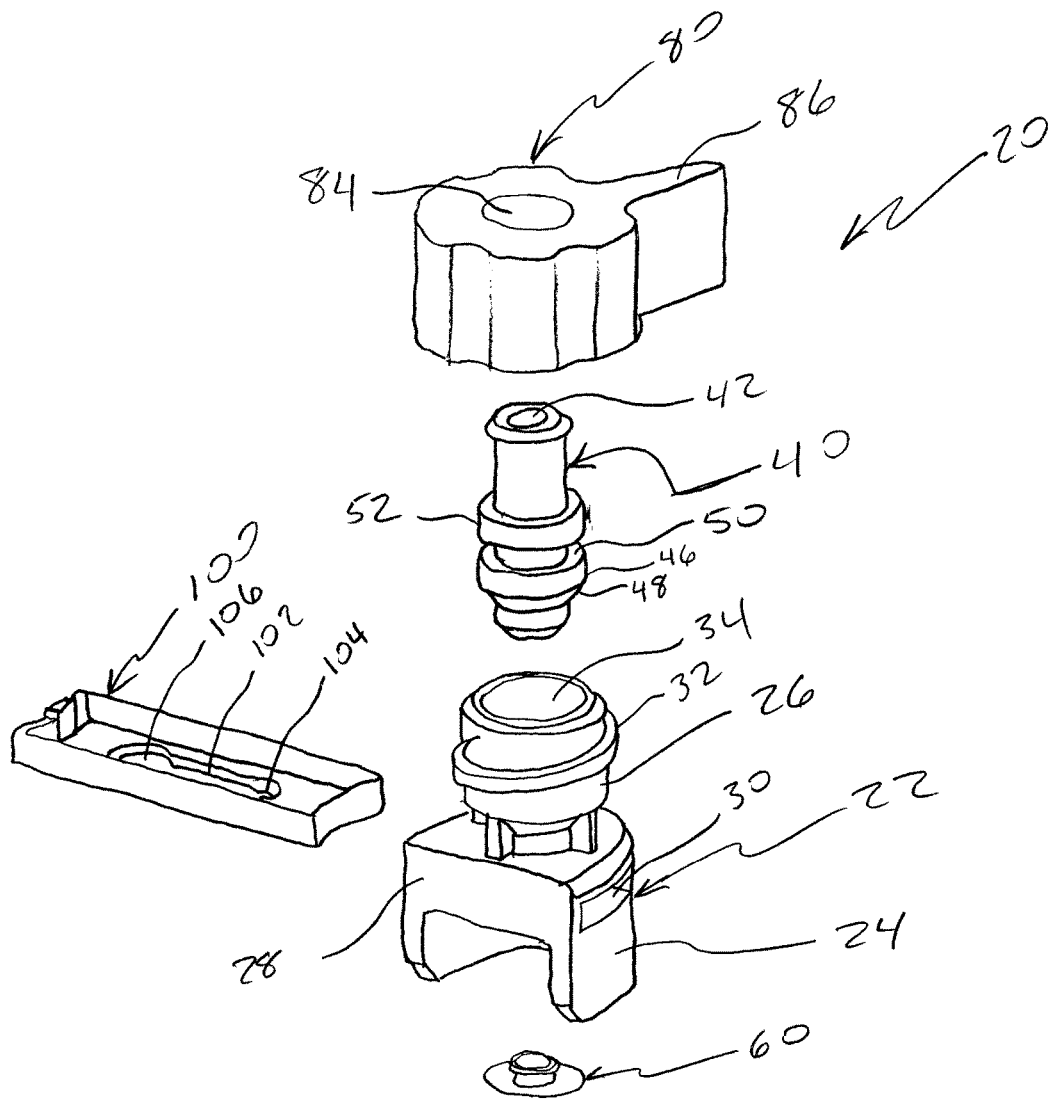
FIG. 3 is an exploded perspective view of an embodiment of a bronchoscope adapter of the present invention.
Figure 4:
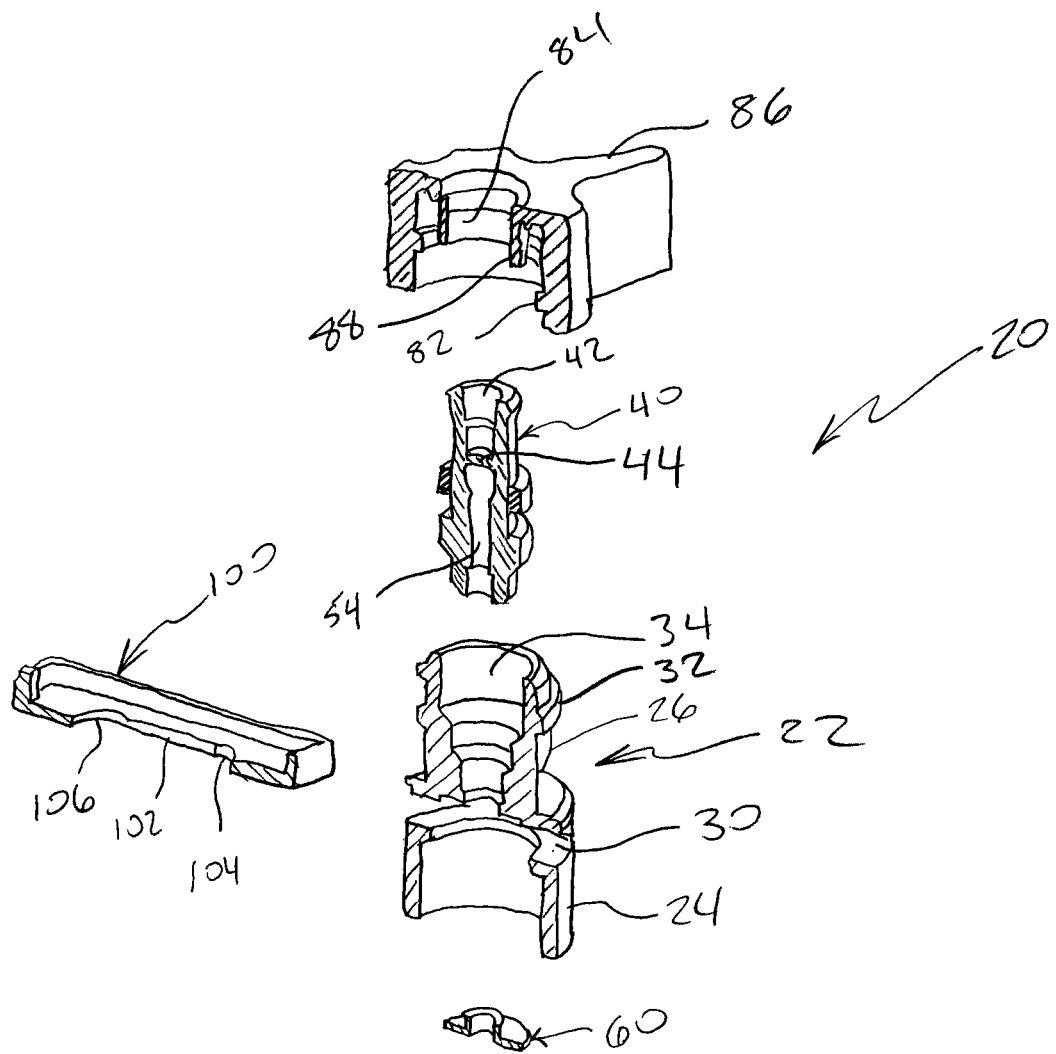
FIG. 4 is an exploded cutaway perspective view of the bronchoscope adapter of FIG. 3.
Figure 5:
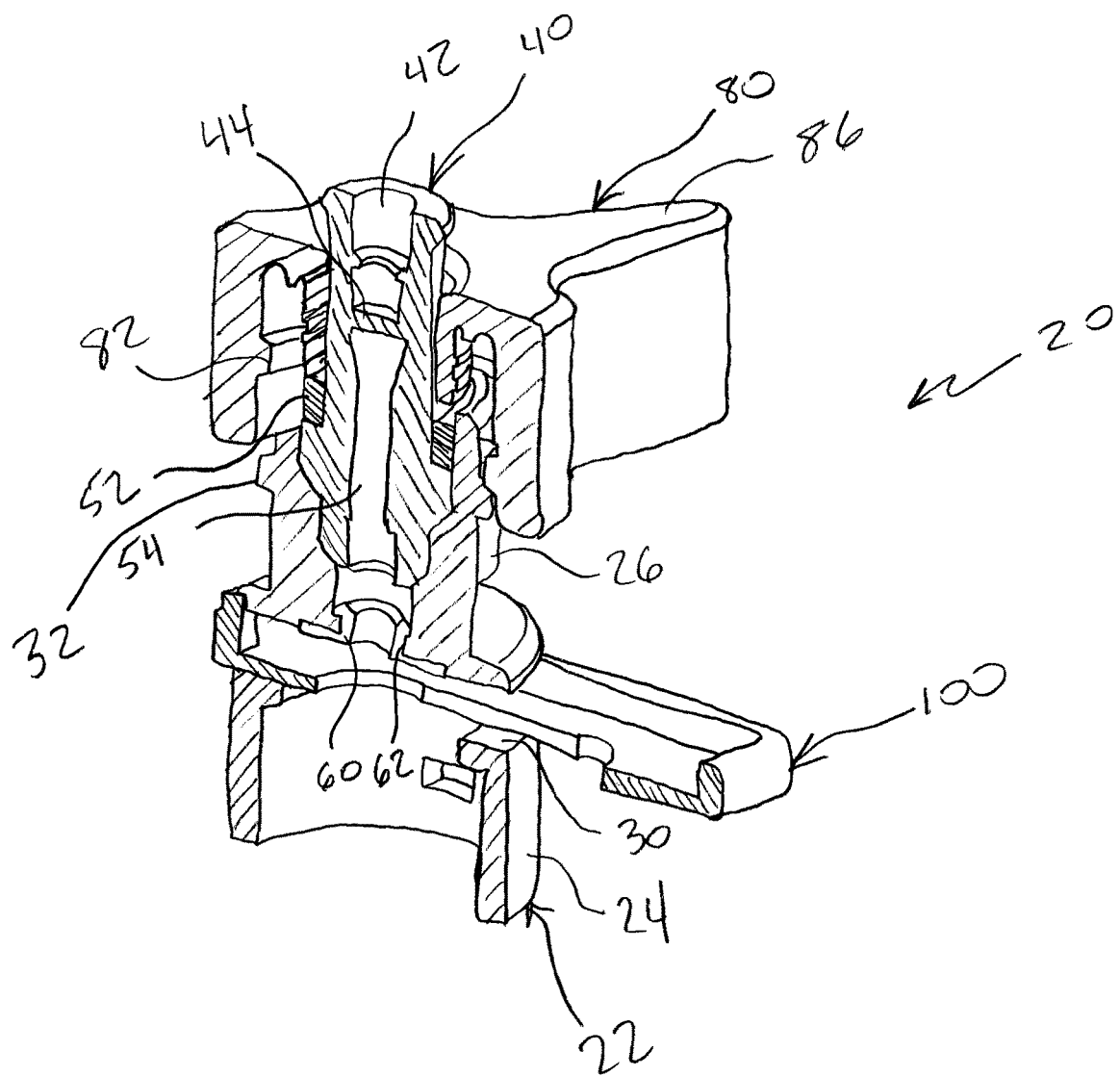
FIG. 5 is an assembled cutaway perspective view of the bronchoscope adapter of FIG. 3.

Referring to FIGS. 3-5, there is shown a bronchoscope adapter 20 of the present invention. The bronchoscope adapter 20 generally includes a housing 22 a clamping block 40, a port seal 60, retainer nut 80, and a slide lock 100.

The housing 22 generally includes a female connector 24 and a male connector 26. The female connector 24 is shaped to fit over the gasket fitting 11 on the access port 2 of a bronchoscope handle. Preferably, the female connector 24 includes an interference surface 28 which abuts against a corresponding surface of the bronchoscope handle and prevents the housing 22 from rotating when it is attached to the access port 2. The female connector 24 also defines a transverse slot 30 through which the slide lock 100 is slidingly housed.

The male connector 26 includes an external thread 32 that engages the retaining nut 80 and defines an inner lumen 34. The male connector 26 mates with the retaining nut 80 and allows the retaining nut 80 to compress the clamping block 40 between the retaining nut 80 and the housing 22.

The clamping block 40 is an elastomeric component constructed of an elastomeric material such as rubber or silicon, or any other appropriate elastomeric material. The clamping block 40 defines an inner lumen 42 and resides partially within the inner lumen 34 of the male connector 26 of the housing 22 and partially within the retaining nut 80. The inner lumen 42 of the clamping block 40 has a first diameter when the clamping block 40 is in an uncompressed state. The first diameter is sized to receive tools used with the bronchoscope. When the retaining nut 80 is tightened against the housing 22, the clamping block deforms, reducing the inner lumen 42 to a second diameter that is smaller than the first diameter such that a seal is formed against the tool.

The inner lumen 42 is interrupted by valve 44, which is elastically biased to a normally-closed state. The valve 44 blocks the passage of air through the clamping block when the access port 2 of a bronchoscope is not in use. When a tool is inserted through the inner lumen 42, the valve 44 is forced out of the way to an open position.

The clamping block 40 may include a beveled collar 46 radiating from its outer wall. The beveled collar 46 includes a beveled surface 48 and a flat surface 50. The flat surface 50 is configured to be acted upon by a spacer ring 52, which is, in turn, acted upon by the nut 80 when tightened. The spacer ring 52 is constructed of a rigid material such that it provides a surface against which the nut 80 may slide when rotated thereagainst. The spacer ring 52 thus reduces the degree to which rotational motion of the nut 80 is transmitted to the elastomeric material of the clamping block 40. The beveled surface 48 acts against a corresponding surface the housing 22 to prevent axial movement of the clamping block 40 when the nut 80 is tightened. The beveled surface 48 also transmits axial compression to an inward deformation of the central lumen 42 such that any tool disposed within the central lumen 42 is squeezed by the clamping block 40. Additionally, the central lumen 42 of the clamping block 40 may include a narrowing 54 to assist in forming a seal around a tool.

The port seal 60 is an elastomeric gasket that allows the female connector 24 of the housing 22 to form a seal against the gasket fitting 11 of the access port 2. The port seal 60, preferably, is shaped to snap-fit into a correspondingly shaped lip 62 of the housing 22. The seal 60 may be formed of the same material as the clamping block 40. The seal 60, however, is separate from the remaining components of the adapter 20. Separating the seal 60 from the rest of the adapter 20 further isolates any rotational force imparted by the retaining nut 80. This isolation ensures the seal between the bronchoscope adapter 20 and the access port 2 is not compromised. This isolation also facilitates easy turning of the nut 80.

The retaining nut 80 is a female component that has an internal thread 82 that corresponds to the thread 32 of the housing 22. The retaining nut 80 also forms an inner lumen 84 that receives a portion of the clamping block 40. Preferably, the inner lumen 84 is partially defined by an inner sleeve 88 that extends downwardly from the top of the retaining nut 80 and slides inside the inner lumen 34 of the housing 22 when the retaining nut 80 is mated with the housing 22. The inner sleeve 88 acts upon the spacer ring 52, which in turn presses the flat surface 50 of the beveled collar 46 of the clamping block 40. The retaining nut 80 also includes an extension 86 that allows the nut 80 to be rotated with a single finger or thumb.

The slide lock 100 is constructed of a rigid or semi-rigid material and defines a longitudinal slot 102 that has a small circular end 104 and a larger circular end 106. The slide lock 100 is slidingly contained within the slot 30 of the housing 22. The larger circular end 106 is large enough to pass over the gasket fitting 11 of the access port 2 of the bronchoscope handle 4. Once in place over the gasket fitting 11, the slide lock 100 may be pushed to one side to a locked position whereby the small circular end 104 is engaged around the neck of the gasket fitting 11, thereby locking the housing 22 to the access port 2.

In operation, the ease of use of the improved bronchoscope assembly 20 becomes readily apparent. With one hand, a physician is able to grab the housing 22 of the bronchoscope assembly 20 and place it over the access port 2 of the bronchoscope handle. With one finger, the slide lock 100 is slid to a locked position, thereby securing the bronchoscope assembly 20 to the bronchoscope. Inserting a tool into the working channel 3 through the bronchoscope adapter 20 is also simplified due to the easy-turning design of the nut 80.

Although the invention has been described in terms of particular embodiments and applications, in the context of a bronchoscope and bronchoscopic tools, it should be appreciated that other applications using other type of endoscopes and endoscopic tools also fall within the scope of the present invention. One of ordinary skill in the art, in light of the teaching, can generate embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

I claim:

1. An adapter for a bronchoscope comprising:
   a housing defining a longitudinal inner lumen and a transverse slot;
   a slide lock insertable through the transverse slot of the housing, the slide lock defining a longitudinal slot separating a small circular end from a larger circular end;
   a clamping block having a spacer ring integrally formed thereon, wherein the clamping block is elastomeric and the spacer ring is rigid;
   a retaining nut having a first end and a second end, the first end configured to mate with a portion of the housing and the second end configured to directly engage a portion of the clamping block;
   wherein the larger circular end is sized to fit over a gasket fitting of a bronchoscope access port; and
   wherein the smaller circular end is sized to engage a surface of the gasket fitting.

2. The adapter for a bronchoscope of claim 1, wherein the spacer ring reduces a degree to which rotational motion of the retaining nut is transmitted to the clamping block.

3. The adapter for a bronchoscope of claim 2, wherein the retaining nut comprises an extension usable to tighten the retaining nut with a single finger or thumb.

4. The adapter for a bronchoscope of claim 1, wherein the clamping block further defines an inner lumen, the clamping block secured between the housing and the retaining nut such that tightening of the retaining nut against the housing compresses the inner lumen, reducing a diameter thereof.

5. The adapter for a bronchoscope of claim 1, wherein the clamping block includes a beveled collar having a beveled surface and a flat surface, the flat surface configured to be acted upon by the spacer ring.

6. The adapter of claim 1, wherein the retaining nut includes an inner sleeve that extends inside the housing.

7. The adapter of claim 1, wherein the clamping block is formed from an elastomeric material.

8. The adapter of claim 1, wherein the transverse slot extends an entire transverse length of the housing.

* * * * *